United States Patent [19]

Kohler, Jr.

[11] 4,130,120

[45] Dec. 19, 1978

[54] BATHING CHAMBER

[75] Inventor: Herbert V. Kohler, Jr., Kohler, Wis.

[73] Assignee: Kohler Co., Kohler, Wis.

[21] Appl. No.: 786,067

[22] Filed: Apr. 11, 1977

[51] Int. Cl.$^2$ .......................................... A61H 33/06
[52] U.S. Cl. ................................................. 128/373
[58] Field of Search ................ 128/373, 24.2, 66, 371, 128/366, 395

[56]    References Cited
U.S. PATENT DOCUMENTS

| | | | |
|---|---|---|---|
| 1,059,314 | 4/1913 | Petter | 128/366 |
| 1,643,528 | 9/1927 | Thurston | 128/366 |
| 1,827,530 | 10/1931 | Le Grand | 128/373 |
| 2,097,952 | 11/1937 | Lohr | 128/66 |
| 2,292,666 | 8/1942 | Schurtz | 128/366 |
| 3,826,250 | 7/1974 | Adams | 128/24.2 |

Primary Examiner—Lawrence W. Trapp
Attorney, Agent, or Firm—Quarles & Brady

[57] ABSTRACT

A bathing chamber is shown having an interior in which the user may lie in the prone position. The chamber has a variety of conditioning elements such as heat and sun lamps, shower sprays and warm air blowers that are sequenced in operation to provide a number of different environmental conditions within the chamber during a single bathing period.

13 Claims, 19 Drawing Figures

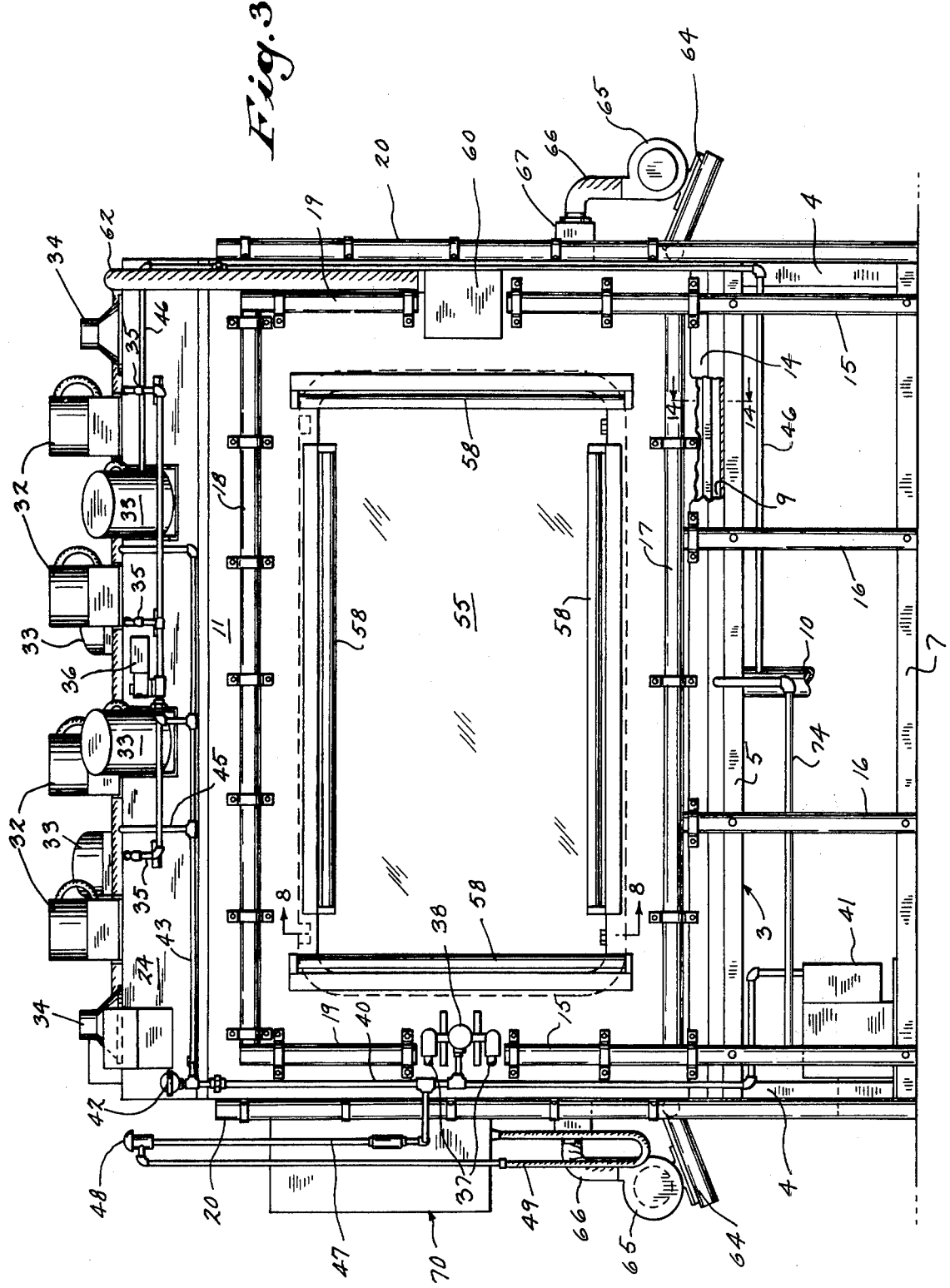

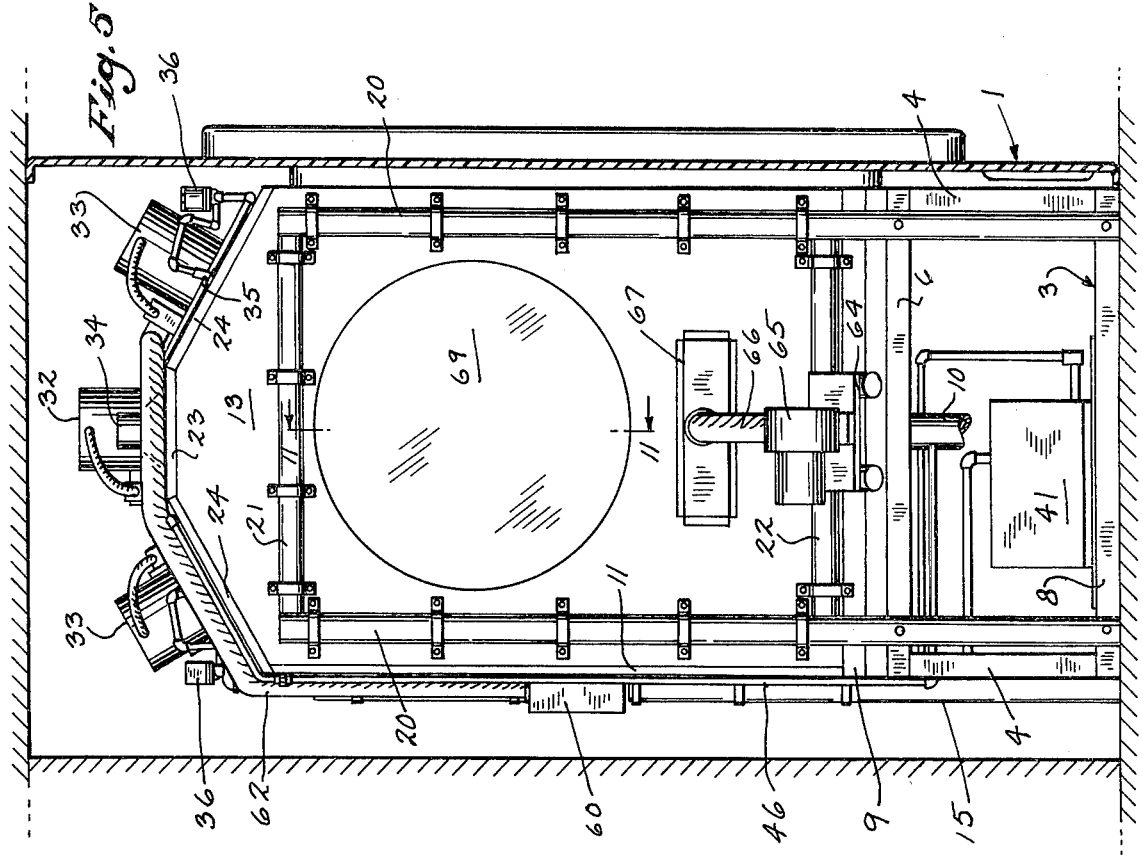
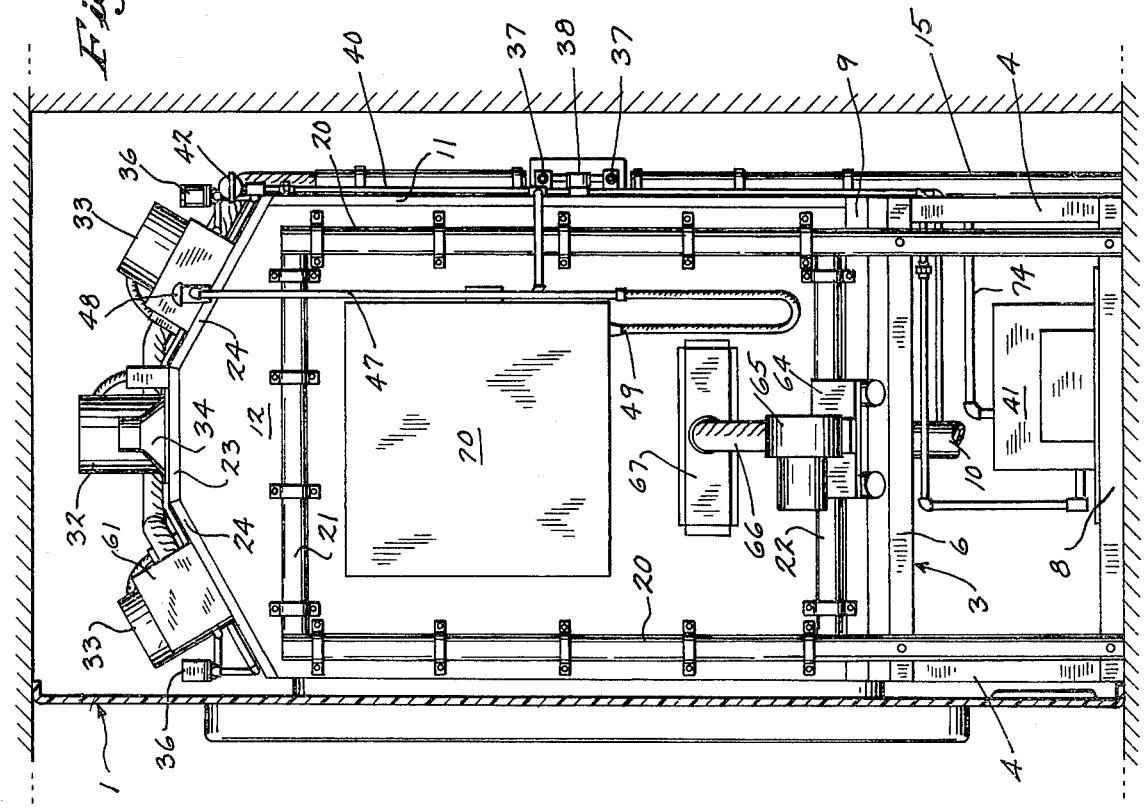

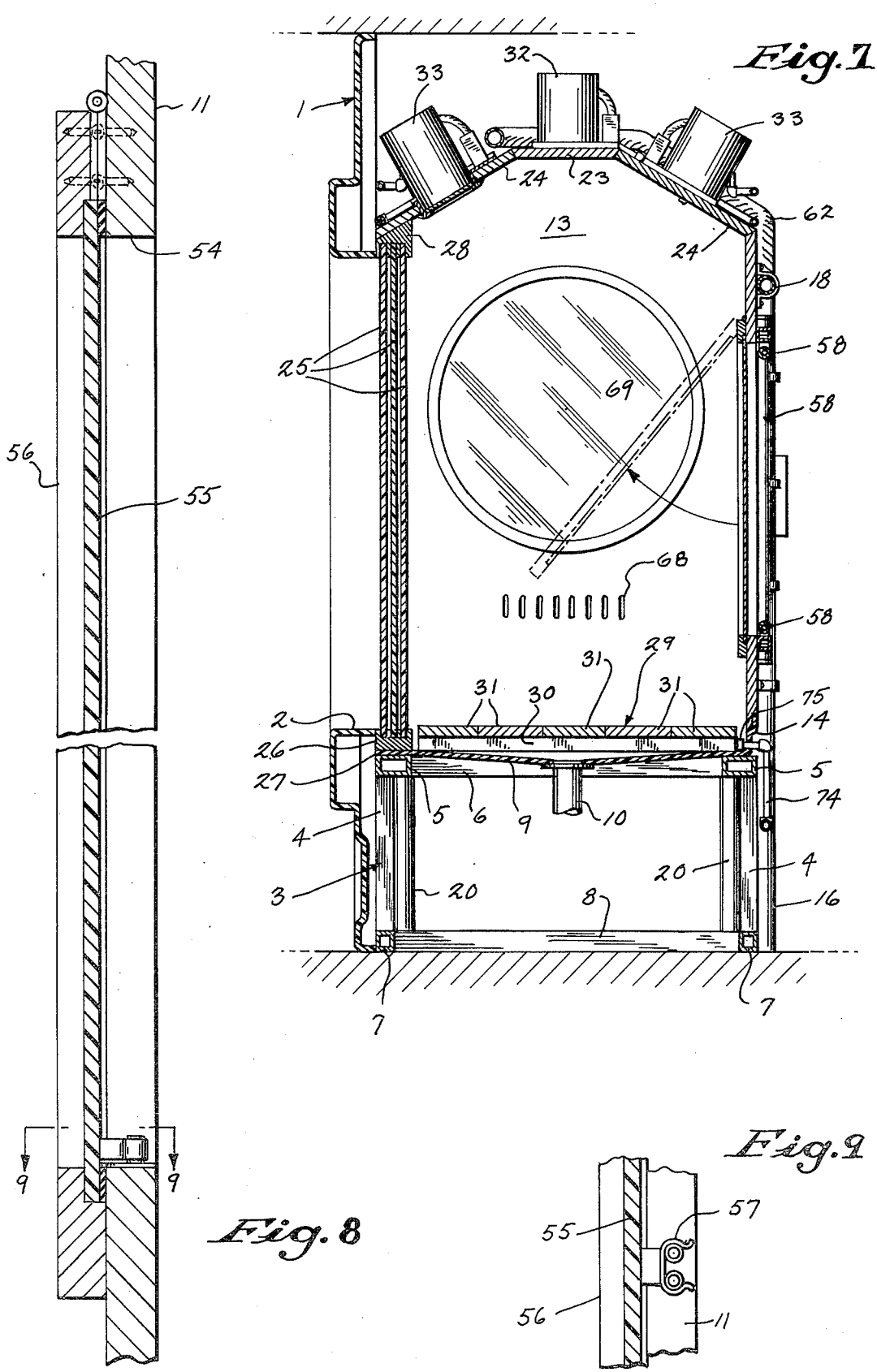

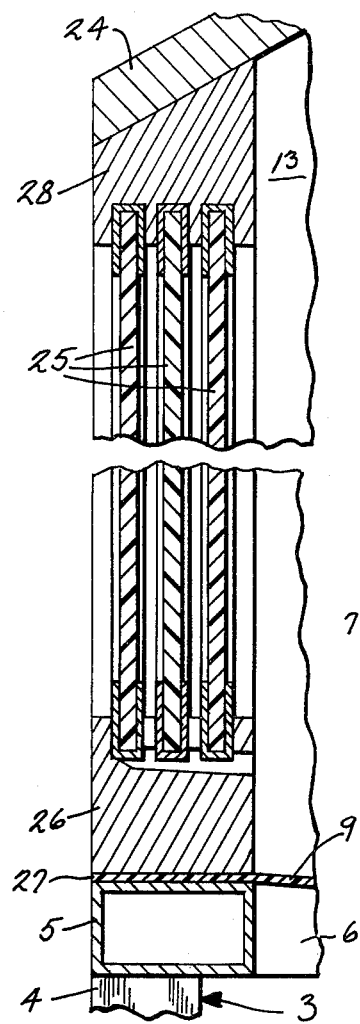
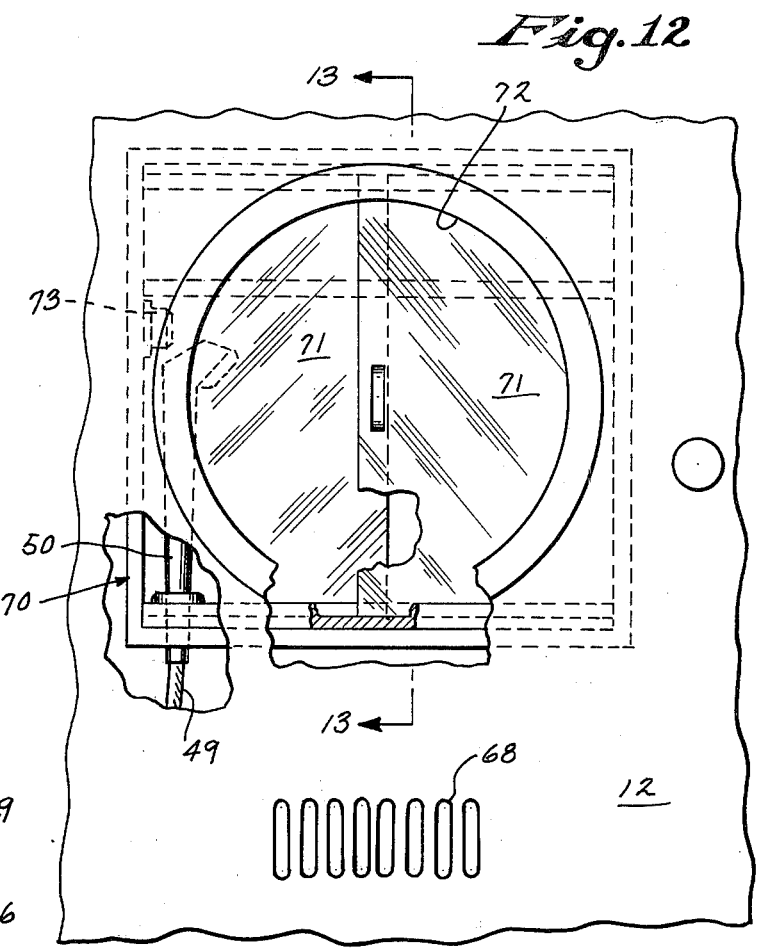
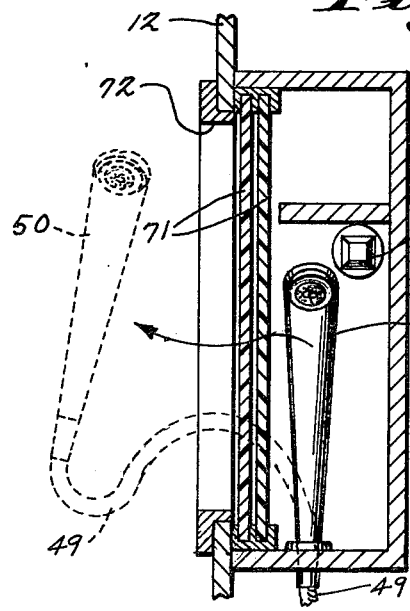
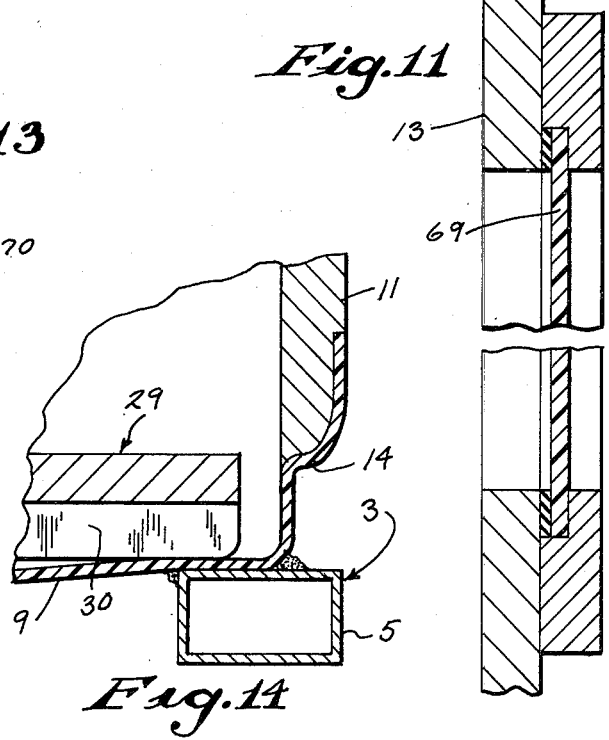

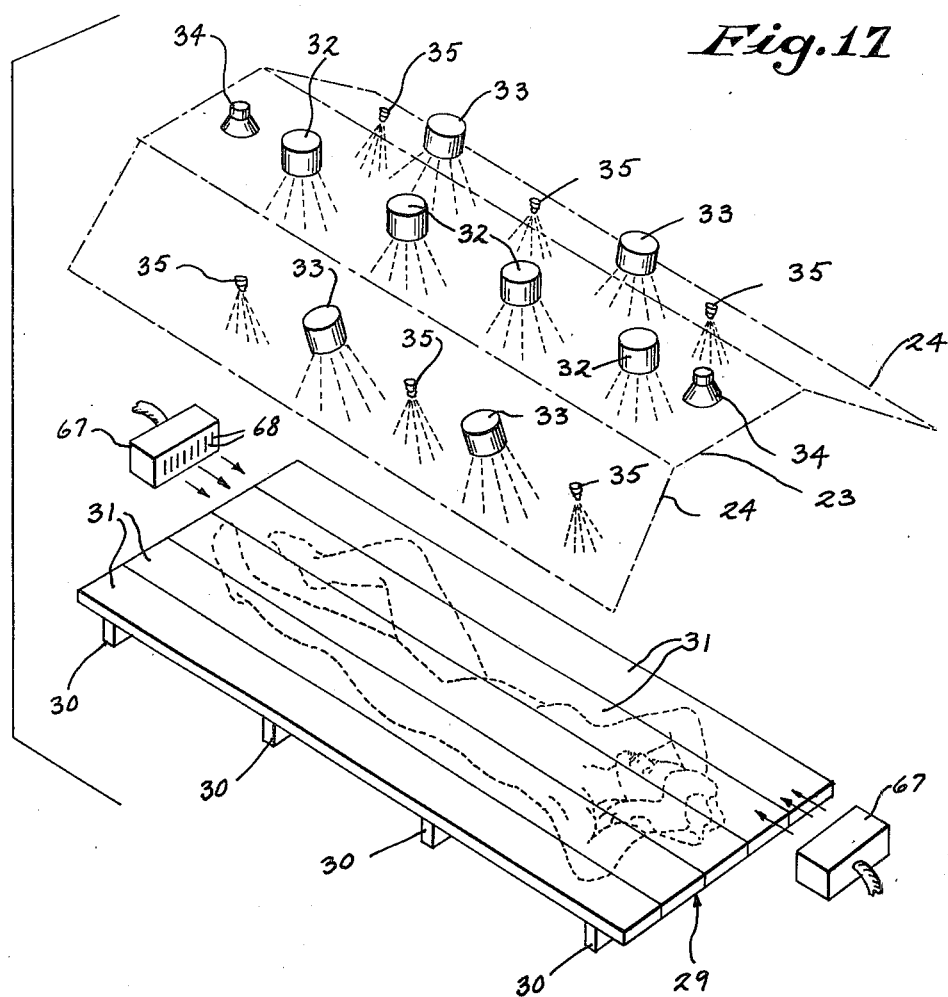
Fig.17
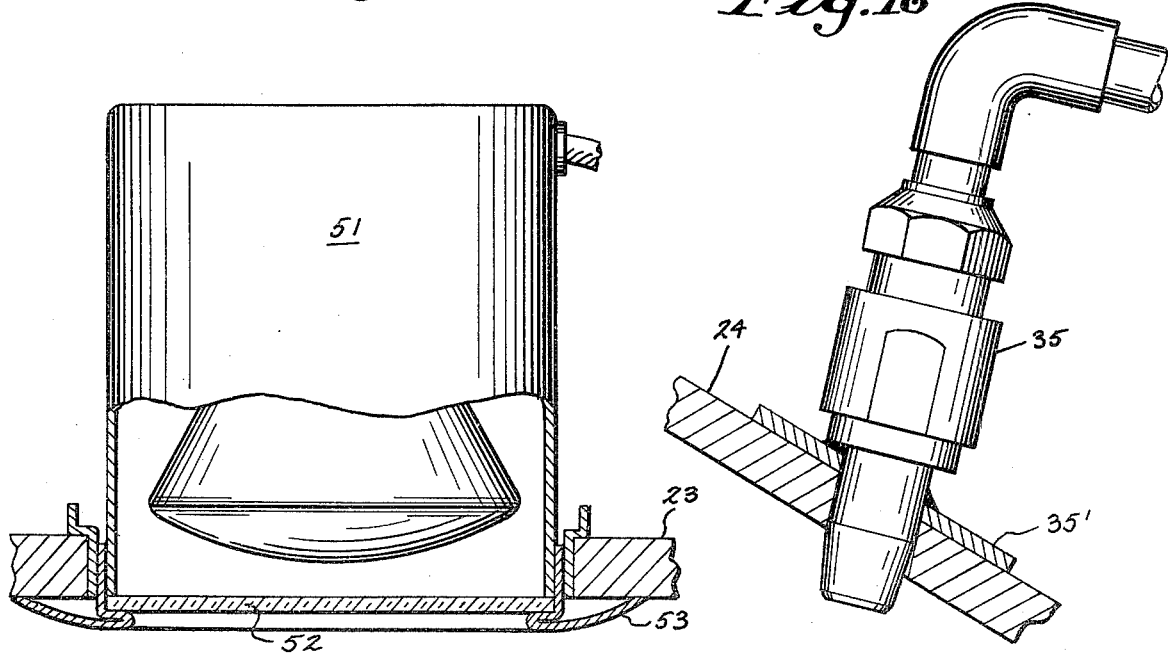
Fig.15
Fig.16

BATHING CHAMBER

BACKGROUND OF THE INVENTION

1. Field of the Invention

The present invention relates to a bathing chamber that presents a number of different bathing conditions in a sequence of operation.

2. Prior Art

Baths and bathing have been from early times considered one of the more pleasurable past times important to one's well being. The Roman bath, hot and bubbling baths, the sauna, sun bathing and steam baths are examples of the many forms bathing may take. Man has enjoyed the pleasures of bathing since earliest writings. Early references to bathing appear in the Bible (Leviticus 16, 17; Number 19) and built-in bath and drainage systems have been found in Greek ruins more than 3,000 years old. The Romans are well known for their large public baths, and mineral baths and spas have long been associated in Europe with fashionable resorts, and also as having therapeutic value for treatment of bodily ailments.

Various attributes are described for bathing, usually reflecting the user's personal reaction to and notions of the effect of the bath. It is variously described as relaxing, reducing tensions, invigorating, relieving soreness or strain, or just simply as enjoyable and pleasurable. The sun gives warmth and a satisfaction from tanning the body. The warm environments of the sauna, steam bath and hot room have their special effects, and water bathing in a tub or shower with hot or cold water induce their own particular effects upon the bather.

Normally, only one form of bath is experienced at a time. The steam bath, for example, has its own special room for entering and sitting, or box in which the body is enclosed with the user's head protruding. The sauna bath similarly has a specially made chamber with its unique wood interior and splashing of water on hot rocks or stove. Heat and sun lamps are unitary devices, and the many forms of tubs and whirlpool arrangements are constructed with but one form of bath in mind.

There has been some suggestion of combining different bathing functions into a single apparatus. In Carlson, U.S. Pat. No. 1,985,147 an ordinary bathing tub is extended upward to form a chamber. A shower spray is provided and also a steam inlet for medicinal, vapor treatment. The patent mentions the use of hot air and electrical heating apparatus in combination with the bathing unit, but does not disclose how to incorporate these features into the equipment. Renstrom, in U.S. Pat. No. 585,344 placed a couch beneath a shower and a mist emitting device, and also provided for electrical therapy in what he termed a hygiene apparatus. Compton, in U.S. Pat. No. 3,587,118 shows a shower stall with a built-in seat and hot air blowers leading into the stall to circulate air of a comfortable temperature for drying the user. These various devices are oriented toward therapeutic treatment for patients, rather than the creation of baths to be used on a regular basis by normally healthy persons for securing the multiple advantages of a variety of different bathing environments.

SUMMARY OF THE INVENTION

The present invention resides in a bathing apparatus that provides a series of different environments in a sequence of operation, such apparatus having a chamber enabling the user to rest in a fully prone position, a plurality of interior conditioning elements such as lamps, shower spray, steam injection and air blowers all arranged in a programmed circuit to automatically create a succession of bathing conditions.

The variety of benefits derived from widely different forms of bathing conditions are incorporated in a single apparatus. The synergy experienced by the user from multiple forms of bathing as in infra-red and ultra-violet light, steam, showers and drying wind can all be obtained in one bath from one apparatus. There is thus combined into a single unit that may be installed in the home, club or other location a full range of bathing experiences.

The apparatus is tastefully designed and of aesthetic appearance. The user thus has a sense of luxury and visual enjoyment, to match and accompany the benefits and sensual satisfaction of bathing. It is a particular purpose to make bathing a treat, rather than as a treatment for medical reasons.

It is an object of the invention to provide a bathing apparatus that creates a succession of different environmental conditions in automatic sequence, to gain a synergy of different relaxing and stimulating conditions.

It is another object to provide for the prone position in the use of a bathing apparatus, so that the body in a relaxed state can be exposed uniformly to each of a variety of conditions.

It is another object to expose a bather to a number of entirely different conditions, such as sun, rain, steam and wind to obtain a maximum of different stimulating hygienic conditions in a single bath.

It is a still further object to provide a bathing structure in which a variety of fittings are attached to the exterior of a chamber in a manner that there is ready access to them for adjustment, repair or replacement.

It is a further object to provide a bathing chamber that can be shipped in fully assembled condition, or in a knocked down condition easily assembled at the place of use.

It is a further object to provide a bathing chamber that is strong and durable which may be easily installed at a construction site.

The foregoing and other objects and advantages of the invention will appear from the following description. In the description reference is made to the accompanying drawings which form a part hereof, and in which there is shown by way of illustration a preferred embodiment of the invention. Such embodiment does not necessarily represent the full scope of the invention and reference is made to the claims herein.

BRIEF DESCRIPTION OF THE DRAWINGS

FIG. 3 is a rear view of the bathing chamber, FIG. 4 is a right hand end view of the bathing chamber, FIG. 5 is a left hand end view of the bathing chamber, FIG. 7 is a view in cross section of the bathing chamber in the plane 7—7 indicated in FIG. 2, FIG. 8 is a partial view in cross section of the rear wall of the bathing chamber in the plane 8—8 indicated in FIG. 3, FIG. 9 is a fragmentary view in cross section showing a catch in the rear wall of the bathing chamber that is taken in the plane 9—9 indicated in FIG. 8, FIG. 10 is a fragmentary view in cross section in the plane 10—10 indicated in FIG. 1, to show the three sliding doors at the front of the bathing chamber, FIG. 11 is a fragmentary view in cross section of the left hand end wall of the bathing chamber in the plane 11—11 indicated in FIG. 5 to show the window mounted in such end wall, FIG. 12 is a fragmentary view in elevation of the inside of the right hand end wall of the bathing chamber showing a cabinet mounted in the end wall, FIG. 13 is a fragmentary view in cross section of the cabinet of FIG. 12 taken in the plane 13—13 indicated in FIG. 12, FIG. 14 is a fragmentary view in cross section taken in the plane 14—14 indicated in FIG. 3, FIG. 15 is a view with parts broken away of a lamp construction in the roof of the bathing chamber, FIG. 16 is a view in cross section of a spray nozzle construction in the roof of the bathing chamber, FIG. 17 is a schematic representation of the relationship of lamps, sprays and blowers with respect to a person within the bathing chamber.

DESCRIPTION OF THE PREFERRED EMBODIMENT

Figure 1:
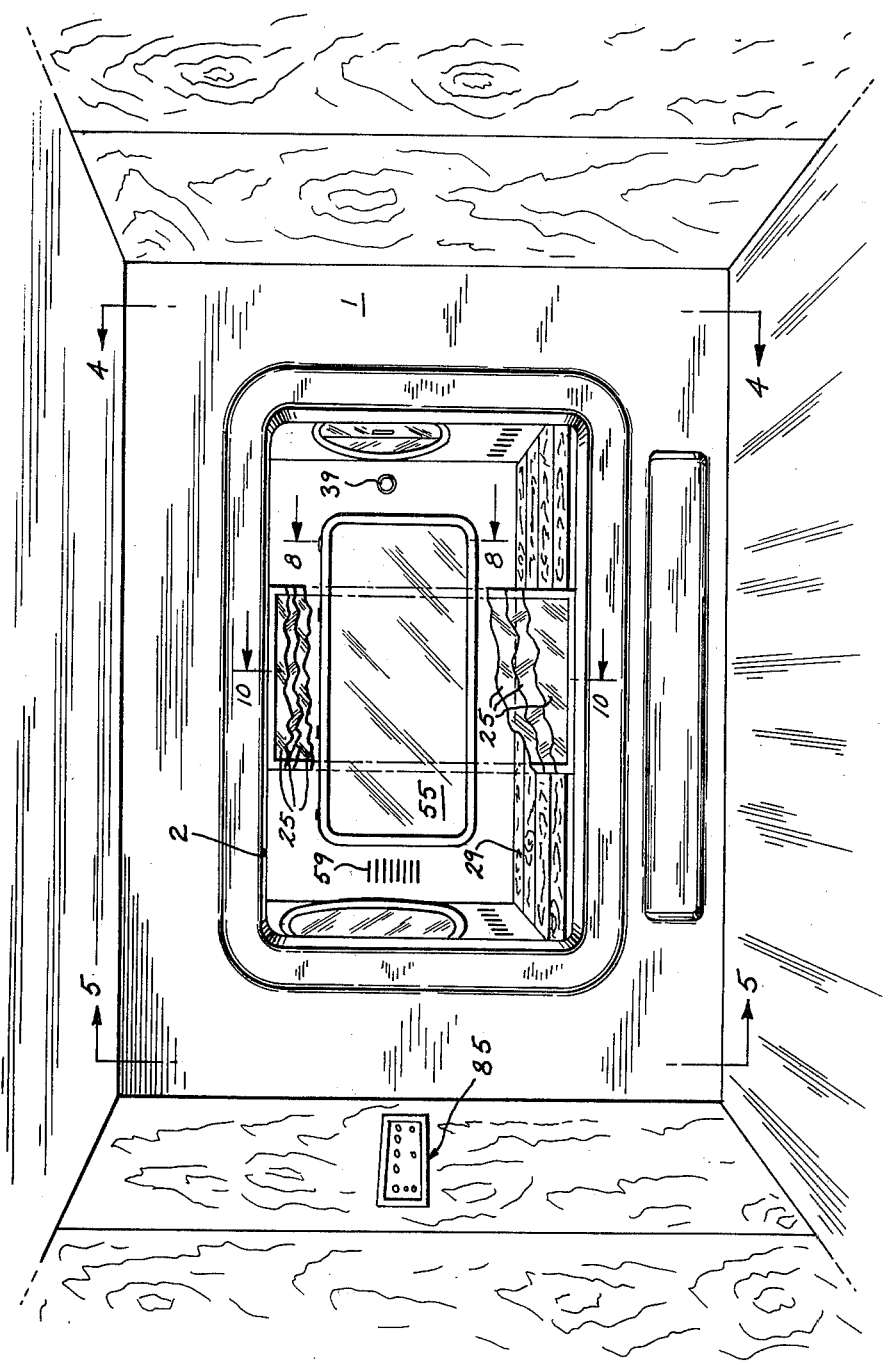
FIG. 1 is a front view of a bathing chamber embodying the present invention as it appears when installed in one end of a room.

Referring now to the drawings, the bathing chamber of the invention may have a decorative front panel 1 of a size that masks from view the equipment comprising the chamber proper. The panel 1 is suitable for installing the chamber in the side of a room as indicated in FIG. 1 and it has a large, framed opening 2 to provide access to the chamber interior. As seen in both FIGS. 1 and 7, the bottom of the opening 2 is raised above the room flooring, and the sides and top of the opening 2 are set well in from the panel edges, so that the panel 1 presents a substantial wall with a central opening that matches the chamber interior that will be described. The panel 1 is shown in FIG. 7 to be of synthetic, molded construction, but it can also be of other suitable form, such as wood paneling.

The apparatus behind panel 1 includes a base stand 3 that is approximately knee height. The base stand 3 is made up of a framework of tubing comprising four corner legs 4 that support a pair of horizontal, lengthwise joists 5 extending along the front and rear of the chamber and a pair of short end joists 6 that are seen in FIGS. 4 and 5. To complete the base stand 3 there are two lengthwise floor stringers 7 which extend between the bottom ends of the legs 4, and two short stringers 8 that run between the bottom ends of the legs 4 in endwise relationship to the chamber.

A chamber flooring in the form of a shallow drainage tray 9 is seated upon the joists 5 and 6. FIG. 14 shows in section an edge margin of the drainage tray 9 resting upon the rear lengthwise joist 5, and the tray 9 is secured tightly in place by a suitable application of an adhesive to form a unitary part comprising the base stand 3 and the drainage tray 9. Tray 9 is slightly dished to collect run-off water at its center, and a drain pipe 10 leads downward and away from the underside of the tray 9.

A rear chamber wall 11 rises upward from the rear margin of the tray 9, and right hand and left hand end walls 12 and 13 similarly rise up from the two opposite end margins of the tray 9. Bottom margins of the rear wall 11 and the right and left hand end walls 12, 13 fit into an upwardly turned flange 14 of the tray 9 in a manner as shown in FIG. 14, where the bottom margin of the rear chamber wall 11 is shown fitted snugly within the flange 14. A suitable adhesive is employed in these joints, and preferably the tray 9 is of a molded synthetic material to facilitate forming the flange 14 to receive the bottom margins of the respective walls 11–13. The chamber walls 11–13 have been in actual practice formed of teak wood for a number of reasons. First, teak wood has a low temperature coefficient of expansion which facilitates the maintenance of tight joints in the construction. The chamber of the invention is subjected to distinct changes in temperature between use and periods of non-use, and it is desirable to maintain tight seams to prevent leakage and escape of water and steam vapor from the chamber, so that surrounding building constructions are not overly subjected to high moisture and humidity. Teak wood also presents a very pleasing construction from the standpoint of appearance and touch, and contains natural oils which inhibit drying and dimensional change. Of course, materials other than teak wood may be employed, and as an example the bathing chamber can be a one piece molded construction of synthetic materials.

The chamber walls 11–13 are reinforced along their exterior sides by tubular bracing that is tightly strapped to the wall surfaces. Referring first to the rear view of FIG. 3, there is shown a pair of tubular leg braces 15 strapped to the lower side margins of the rear wall 11 which extend downwardly to the floor. The downwardly extending portions of the tubular leg braces 15 are bolted to the rear lengthwise joist 5 and the rear lengthwise floor stringer 7, so as to obtain a unitary construction between the rear wall 11 and the framework comprising the base stand 3. Additional leg braces 16 depend from the lower margin of the rear wall 11, and are similarly bolted to the rear lengthwise joist 5 and floor stringer 7. As seen in FIG. 3, a tubular, horizontal wall brace 17 is strapped along the lower margin of the rear wall 11, and a set of upper tubular braces comprising a horizontal brace 18 along the upper margin of wall 11 and side braces 19 along the upper side margins of the wall 11 are strapped in place to complete the reinforcing structure for the rear chamber wall 11.

As shown in FIGS. 4 and 5, the two end walls 12, 13 are similarly braced, each end wall having a pair of upright tubular leg braces 20 that extend from the floor to nearly the top of the wall, an upper horizontal brace 21, and a lower horizontal brace 22. The leg braces 20 are bolted to the end joists 6 and end stringers 8 of the base framework 3 to provide rigidity and strength for the overall construction. The rear wall 11 overlaps the rear, vertical edges of the end walls 12, 13, and these joints are made tight and firm by applying a watertight adhesive between them and screwing the wall 11 to the edges of the walls 12, 13.

The chamber is provided with a roof made up of a horizontally disposed center ceiling panel 23 which runs along the peak of the roof, and a pair of sloping side ceiling panels 24 that slant downwardly and outwardly from the center panel 23, as particularly illustrated in FIG. 7. The three ceiling panels 23, 24 are of teak wood, similarly as the wall members 11–13, and their ends overlap the top, mating edges of the right hand and left hand side walls 12, 13 and the upper edge of the rear wall 11. These joints are secured by screws and a sealing compound, similarly as the rear wall 11 is secured to the vertical edges of the side walls 12, 13. In this manner a tight construction is obtained that is effectively water and humidity tight for the intended purposes. Also, the assembly of these parts can be made in the field at the site of construction, if desired. Thus, the bathing chamber of the invention can be brought through relatively small entryways of existing buildings for assembly and installation.

At the front of the bathing apparatus there are three sliding doors 25. These doors 25 are shown at the center of FIG. 1 one behind the other, and with a portion of each broken away so as to reveal the interior of the chamber. The doors are also shown in fragmentary portions in FIG. 2, and in addition they are seen in cross sections in FIGS. 7 and 10. Each door 25, as shown in FIGS. 7 and 10, is mounted in grooves at its top and bottom for sliding movement, and the doors may be constructed similarly as in known, enclosed shower stalls. To provide a framework for the doors 25 there is a lower sill 26 resting on the front lip 27 of the drainage tray 9 cemented to the lengthwise front joist 5 of the base stand 3. An upper beam 28 fastened to the underside of the front margin of the front ceiling panel 24, as shown in FIG. 7 and 10, provides grooves for receiving and guiding the upper edges of the doors 25. The doors 25 are preferably of translucent material, as commonly found in shower stall constructions, to pass light without the occupants becoming discernible to persons on the exterior. The three doors 25 spread out to cover the entire front of the framed opening 2 to present a substantially watertight barrier between the interior of the bathing chamber and exterior room, while at the same time providing a maximum size entrance for the chamber.

Parts thus described form an enclosed chamber made up of the flooring 9, a rear wall 11, right had and left hand end walls 12 and 13, a ceiling made up of the three panels 23, 24, and the three doors 25. The interior of the chamber is fitted with a platform deck 29 resting upon and overlying the drainage tray 9. This deck 29 may be made of teak wood, or cypress, or other suitable material upon which the user of the bath may recline. It is shallow in height to leave the bulk of the interior of the chamber open for the user. The user will enter through the front opening 2, and may either lie prone upon the platform deck 29, as schematically illustrated in FIG. 17, or sit upon and move about upon the deck 29. The particular deck 29 shown in the drawings is made up of cross braces 30 on its underside to which are attached plankings 31 that are close to one another to fully shield the upper surface of the deck 29 from the region beneath the deck. This construction permits the entry of stream into the chamber from a level below the deck without scalding the user.

A plurality of chamber conditioning elements are mounted in the roof of the chamber to create different interior bathing environments. Spaced lengthwise along the ceiling center panel 23 is a set of four ultra-violet sun lamps 32 which are located so that upon illumination the readiated ultra violet will uniformly cover the surface area of the platform deck 29. Appropriate wiring for the sun lamps 32 is provided, but not shown in the drawings of the chamber, and a control circuit into which this wiring is connected will hereinafter be described. On each of the ceiling side panels 24 there is mounted a pair of lengthwise spaced infra-red heat lamps 33, and they are similarly arranged so that when illuminated the radiation will uniformly cover the surface of the platform deck 29. At each end of the ceiling center panel 23 is an audio speaker 34 directed to the interior of the cabinet, and these speakers 34 may be connected for stereo sound.

The mounting for both types of lamps 32, 33 is shown in FIG. 15. Both the ultra violet sun lamps 32 and the infra-red heat lamps 33 employ an outdoor type cannister 51 with a transparent cover 52 and a rim like mounting escutcheon 53 which fits in an opening in the ceiling with a snug fit, to give a substantially water and humidity tight construction. The cover 52 will be quartz for the sun lamps and pyrex for the heat lamps.

The chamber ceiling also mounts a set of six water spray nozzles 35. Three of the nozzles 35 are spaced lengthwise along the front sloping ceiling side panel 24, and the other three nozzles 35 are spaced lengthwise along the rear sloping ceiling panel 24. The mounting of a spray nozzle 35 is shown in FIG. 16. The head end of the nozzle 35 protrudes through the ceiling and on the outside of the ceiling it is anchored to a plate 35', which in turn is screwed in place on the outside surface of the ceiling panel 24. The spray nozzles 35 are distributed, or spaced across the chamber ceiling so that a water spray ejected therefrom will uniformly cover the surface area of the platform deck 29.

Figure 2:
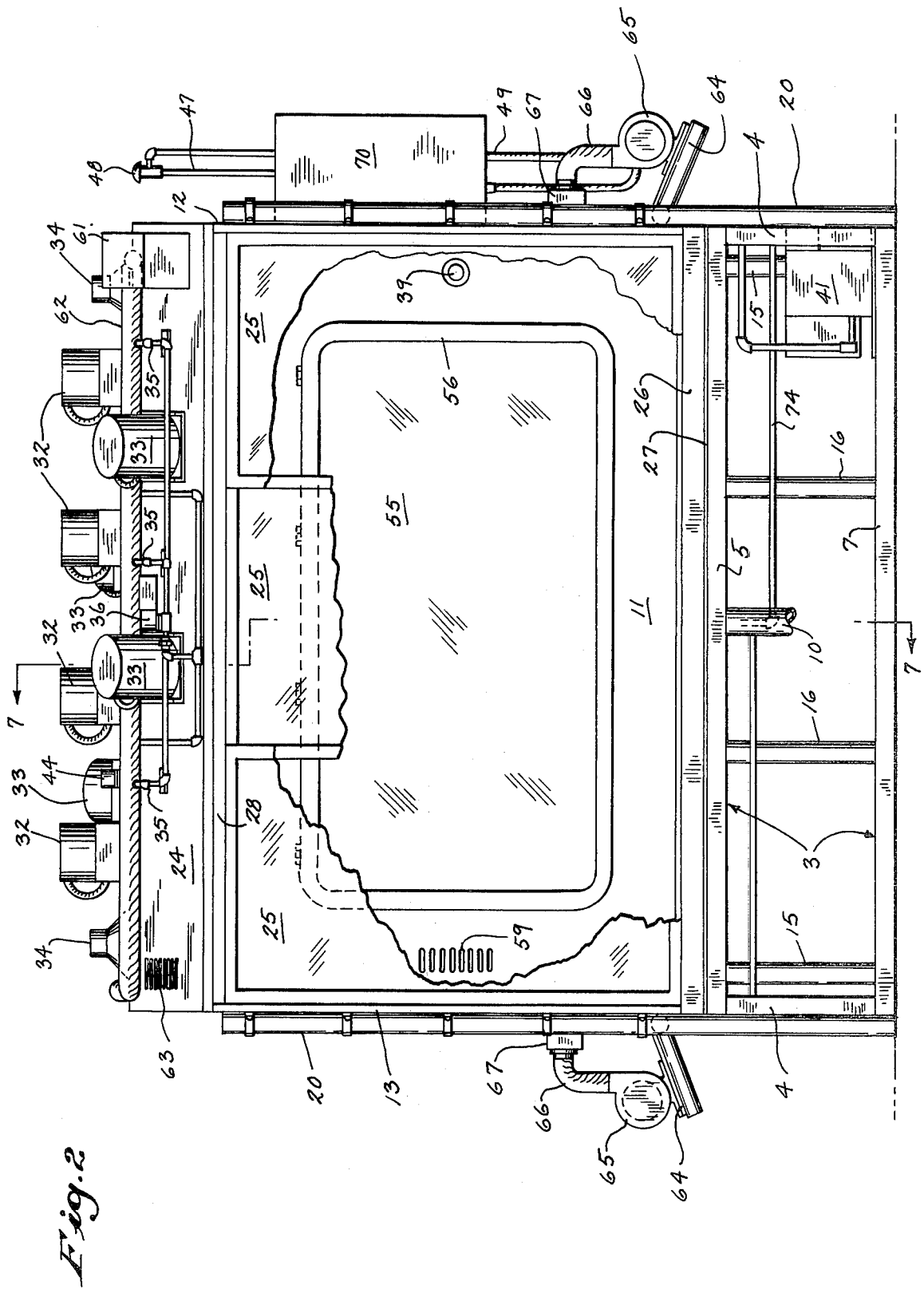
FIG. 2 is another front view of the bathing chamber with the front panel of the chamber removed to disclose construction behind such panel.
Figure 6:
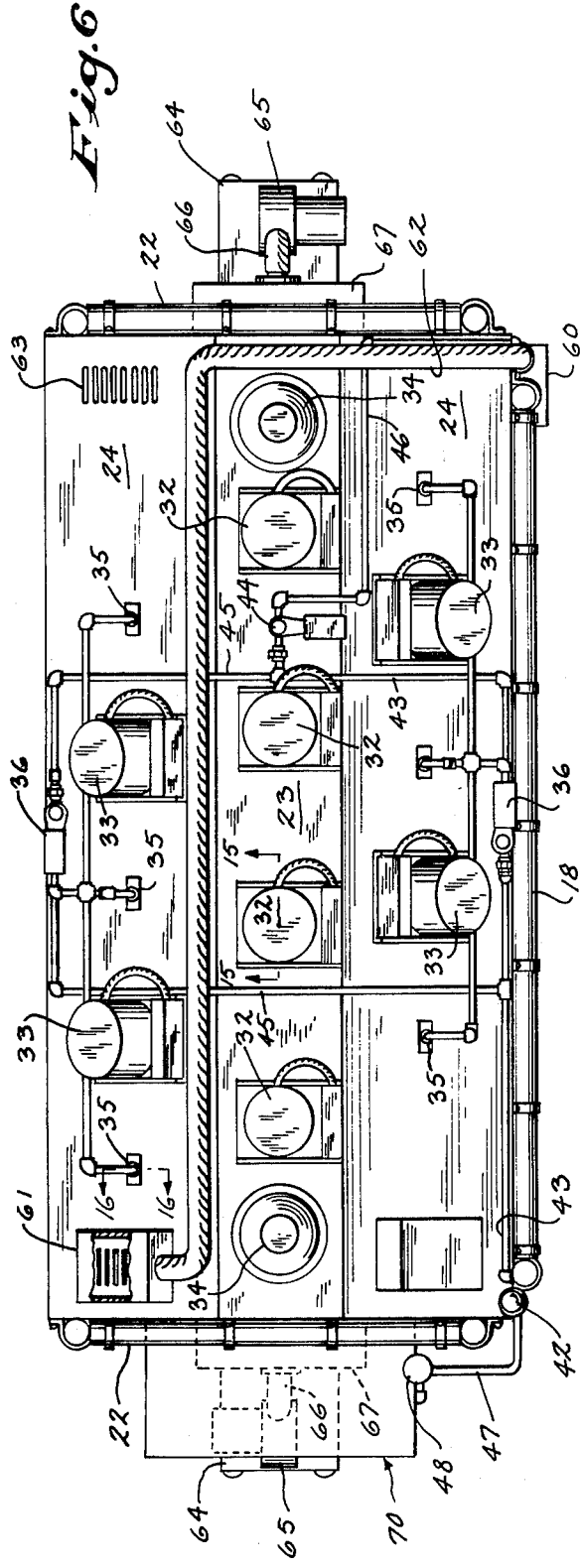
FIG. 6 is a top view of the bathing chamber.
Figure 18:
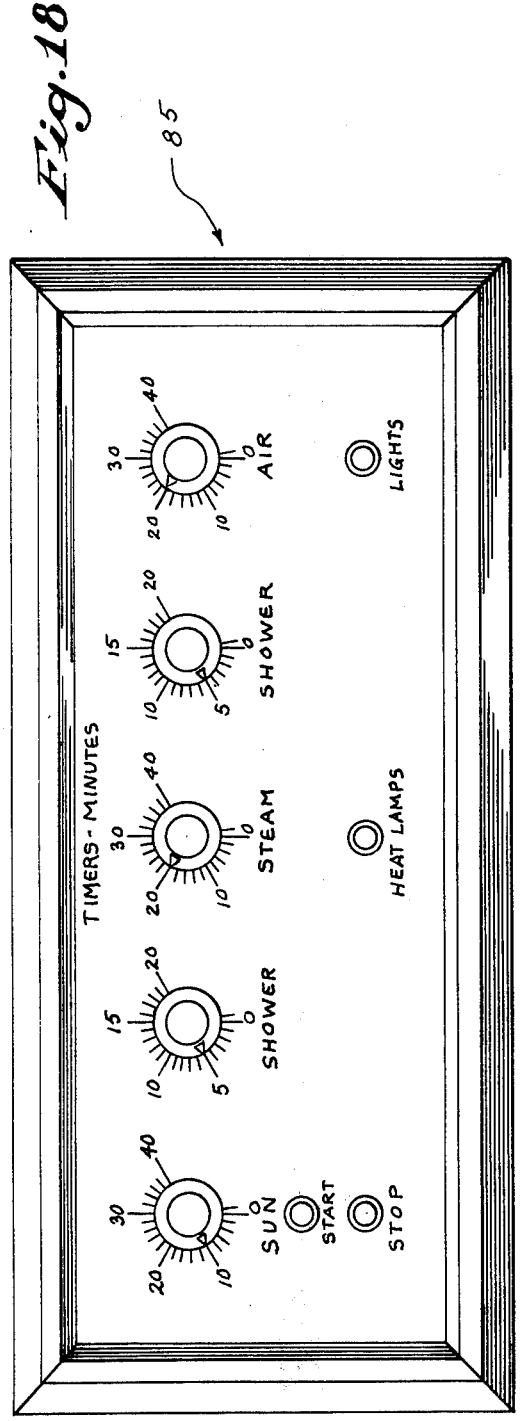
FIG. 18 is a view of a control panel for the bathing chamber.

As shown in FIGS. 2–6, water inlet lines lead to the spray nozzles 35, and these lines include a pair of solenoid valves 36. As particularly shown in FIG. 6, one solenoid valve 36 is disposed atop the front edge of the chamber roof to control the three spray nozzles 35 running along the front part of the chamber, and the second solenoid valve 36 is positioned at the rear edge of the roof to control the three spray nozzles 35 mounted in the rear sloping panel 24 of the ceiling. The water inlet piping can be traced through the apparatus as follows: Referring to FIG. 3, hot and cold inlet lines 37 at the center left of the figure enter a mixing valve 38, which has its manual adjustment handle 39 on the inside of the chamber, as shown in FIG. 2. Water leaves the mixing valve 38 and enters a vertical pipe 40 that extends downwardly to a steam generator 41 and upwardly to an anti-hammer device 42. Referring now to FIG. 6, a feed pipe 43 leaves the anti-hammer device 42 and runs along the rear, exterior edge of the roof. The feed pipe 43 leads to the rear solenoid valve 36, and also extends past the solenoid valve 36 to turn upwardly toward the center of the roof, where there is a connection with a third, pre-conditioning solenoid valve 44. A branch pipe 45 leads off from the feed pipe 43 upwardly and across the roof to the opposite side where it bends to run along the front edge of the roof to make connection with the front solenoid valve 36. The branch pipe 45 also continues past the solenoid valve 36 and returns upwardly across the roof, where it makes connection with the feed pipe 43 and the third solenoid valve 44. From the solenoid valve 44 there is an outlet pipe 46 which runs to one end of the roof, and then downwardly along a rear corner of the chamber, as shown in FIG. 3. At its lower end the outlet pipe 46 turns underneath the flooring 9 to connect to the drain pipe 10. Each of the spray controlling solenoid valves 36 has outlet piping which runs to the respective water spray nozzles 35. One additional plumbing connection for the apparatus comprises a hand shower pipe 47, which branches off from the vertical pipe 40 to pass through a second anti-hammer device 48, and then downward to a flexible hose 49 of a hand held shower 50 shown in FIGS. 12 and 13.

The rear chamber wall 11 has a large, rectangular cutout 54, as shown in FIG. 8, over which is mounted a translucent panel 55. The translucent panel 55 is mounted in a frame 56 which is hinged along its top edge to the inner surface of the rear wall 11. A catch 57, as shown in FIGS. 8 and 9, normally holds the translucent window, formed of the panel 55 and frame 56, in tight engagement with the margin of the cutout 54. The panel 55 ca be swung inwardly to provide access to the space behind the chamber. The panel 55 is translucent in order to conduct light into the chamber from a set of fluorescent bulbs 58 mounted on the rear of the apparatus, as shown particularly in FIG. 3. The emission of light into the chamber interior not only serves the purpose of illumination, but gives the user a feeling of spaciousness. The panel 55 can be either plain or etched, or otherwise decorated to give a pleasing appearance.

As shown in FIGS. 1 and 2, there is a set of parallel openings that form a grillwork 59 in the left hand side of the rear panel 11 to provide for circulation of air. An airbox 60 on the outside of the chamber covers the grillwork 59, as seen in FIGS. 3 and 5, and on the right hand, forward corner of the roof is a second airbox 61 which covers a similar grillwork in the chamber ceiling. An air duct 62 leads from the box 61 lengthwise across the exterior of the roof, and then across the upper edge of the roof and downwardly along the rear wall of the chamber to the first air box 60. Thus, there is provided a means for circulating the air within the chamber, and if desired a low velocity fan can be placed in either of the two air boxes 60, 61 to cause a controlled air circulation. A third grillwork 63 in the front left hand corner of the roof (see FIG. 2) provides an opening from the interior of the chamber to the exterior to relieve the chamber from any pressure build-up that might otherwise occur by reason of circulating air into the chamber in a manner that will now be described.

Referring to each of the chamber end walls 12 and 13, a small platform 64 that extends angularly outward from the chamber is mounted upon the lower horizontal brace 22. Mounted on each platform 64 is an electric blower 65 that has an outlet duct 66 leading into a small plenum chamber 67. An electric heater, not shown, is housed in each duct 66, and each plenum chamber 67 is mounted directly upon the associated end wall 12, 13. Air flows from the chambers 67 through grills 68 into the chamber interior. Each grill 68 comprises a series of closely spaced vertical openings cut into and extending through the respective end wall 12, 13, as shown in FIGS. 7 and 12. The two grills 68 are at a level above the platform deck 29 approximately a distance equal to the height of the upper surface areas of a person lying prone on the platform deck 29. Thus, when the electric blowers 65 are in operation heated air will be directed into the chamber through the grills 68 to cause a flow of warm drying air across the body of the occupant.

Each of the chamber end walls 12, 13 includes auxiliary equipment located above the air inlet grills 68. The left hand end wall 13, as seen in FIGS. 7 and 11, has a framed, circular window 69. The window 69 can take any of several forms. It can be transparent, so that a user of the bathing chamber has a view of the exterior, or it may be frosted, or contain a design to give a pleasing appearance, or a further alternative is to provide for the mounting of plants, or some other object, outside the window to increase and enhance the aesthetics of the bathing chamber.

Attached to the exterior side of the right hand end wall 12 is a protruding, generally rectangularly shaped cabinet 70. The cabinet 70 presents to an occupant a pair of sliding acrylic doors 71, as seen in FIG. 12, and these doors 71 close over a circular, framed cabinet opening 72 cut into the right hand chamber wall 12. The cabinet 70 is shown in cross section in FIG. 13, and it is seen that it is provided with a shelf and floor to receive bathing articles and toiletries, and it also houses the hand held shower 50 that may be withdrawn from the cabinet 70. An off-on and control handle 73 is in the wall of the cabinet 70 adjacent the shower head 50 for operating the shower. The shower 50 can be grasped by the user and pulled out the opening of the cabinet 70 into the bathing chamber by taking up the flexible hose 49 which enters through the bottom of the cabinet 70.

The bathing chamber has a steam line 74 running from the steam generator 41 that enters the chamber through the flange 14 of the drainage tray 9 at the middle rear of the chamber. As illustrated in FIG. 7, there is a steam nozzle 75 which is at a level beneath the top surface of the platform deck 29, so that steam entering the chamber will not flow directly upon the user. Rather, steam may circulate upward along the rear wall 11, and also under the deck 29 to the front edge and then upwardly along the doors 25.

As hereinbefore stated, the electrical wiring for the bathing chamber has not been shown in FIGS. 1–18. The physical wiring is usual in nature, except for the governing circuit, shown in FIG. 19, that sequences the operation of the chamber conditioning elements comprising the ultra violet sun lamps 33, the shower nozzles 35, the steam generator 41, and warm air blower-driers 65.

Figure 19:
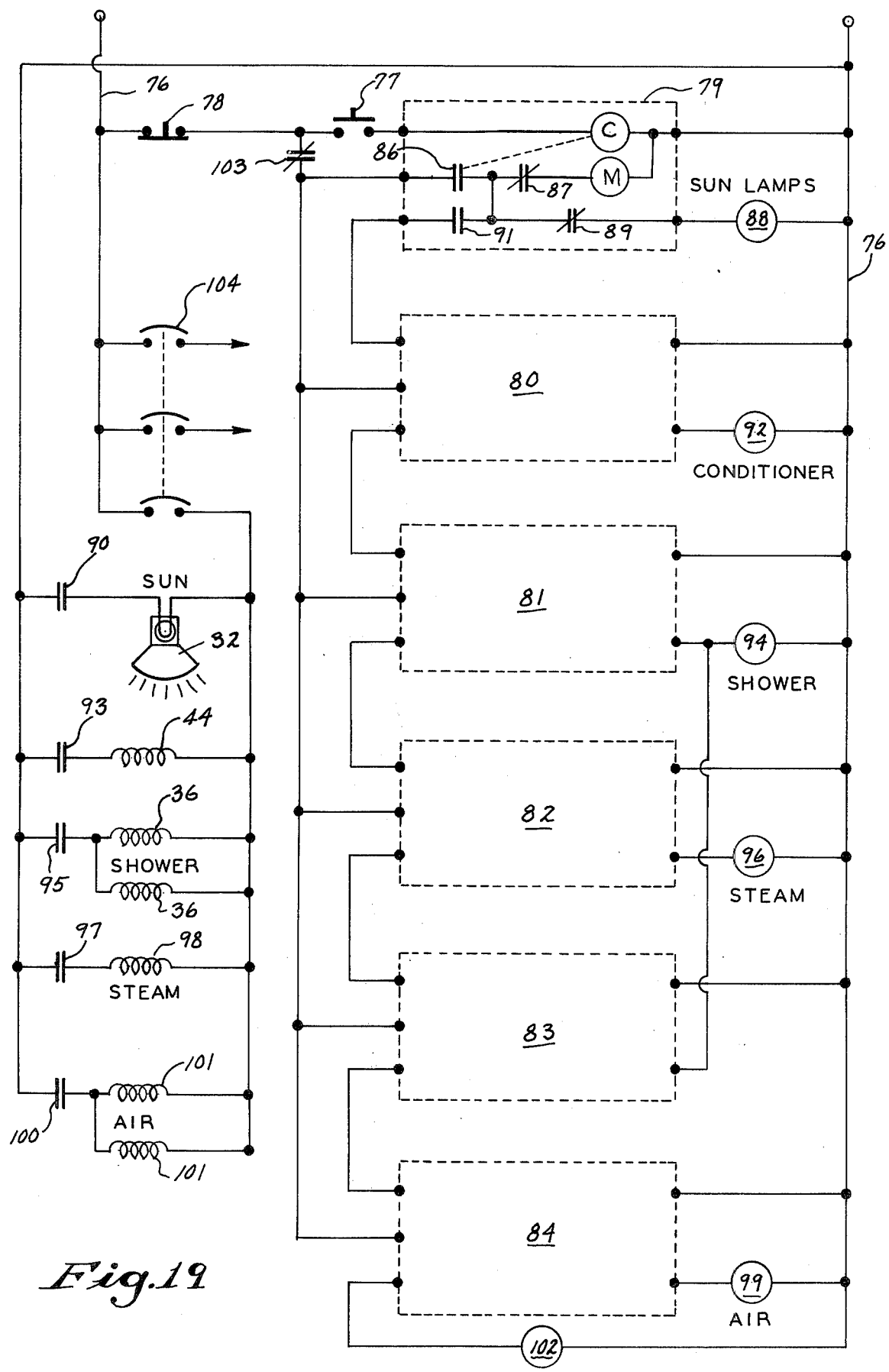
FIG. 19 is a schematic wiring diagram of a control circuit for the bathing chamber.

In FIG. 19, there are voltage input lines 76 feeding a control circuit at the right hand side of the drawing, which circuit has a start button 77 and a stop button 78 in series between the lines 76. A bank of six, like motor driven timers 79 through 84 are arranged between the input lines 76, and since they are alike only the interior connections of the timer 79 are shown. The timer 79 controls the length of time the sun lamps 32 will be on, and this time is pre-set by the user by adjusting the first timer knob on the control panel 85 of FIG. 18. The timers 80–84, for shower, steam, shower and drying air, respectively, are also pre-set by the user before entering the bath, so that the automatic sequencing of changing conditions in the chamber during a single bathing period is at the control of the user.

The operation of the timer 79 will first be described, and then the chain of automatic control over the sequential development of different bathing conditions in the chamber. Upon depression of start button 77 a clutch coil C in the timer 79 is energized and normally open contacts 86 associated with coil C close. This places motor coil M across the control voltage lines through normally closed contacts 87, so that the timer motor runs. Clutch coil C remains energized through the self-holding contacts 86 after the start button 77 is released. Sun lamp control relay coil 88 is also energized through a second set of normally closed contacts 89, and the relay coil 88 closes sun lamp contactor 90 shown in the power circuit at the left hand side of FIG. 19. The sun lamps 32 are then energized.

Upon the timer motor M running to the end of the pre-set time, normally open contacts 91 associated with the motor M close, to feed control voltage to the second motor driven timer 80. Also, the contacts 87, 89 associated with motor M open to (i) turn off the sun lamps, by deenergizing the control coil 88, and (ii) shutting off the motor M. Clutch associated contacts 86 also open, to reestablish the turned-off at-rest condition of the timer 79. This internal operation of the motor driven timer 79 is standard, and the timers used in the invention are commercially available.

The timer 80 now operates through the same type of cycle as did timer 79. It controls the solenoid valve 44 on the roof of the chamber by energizing a water conditioning control relay coil 92, which then closes its contactor 93 in the power circuit. Thus, the valve 44 opens to draw water through the pipe system leading to the spray nozzles 35, and ejects this water through the pipe 46 to the drain 10. This ensures that hot water is fed into the piping, so that when the showers 35 are turned on the water is pre-conditioned to the anticipated temperature, as set by the manual mixing valve 38.

The timer 80 next causes the timer 81 to operate, and in the circuit shown this is for a shower, or spray condition. The shower control relay coil 94 is energized to close contactor 95, which in turn establishes a circuit for the two shower solenoids 36. The showers will now run for their pre-set time, and next the timer 82 is operated for a steam environment within the chamber.

For turning on the steam, a relay coil 96 is energized by the timer 82. The coil closes its contactor 97 to energize a valve coil 98 in the steam generator. After the steam sequence, timer 83 is run to control a second spray, or shower environment. Then, the final chamber condition of dry wind from the body-height grills 68 is controlled by the timer 84. In this sequence control relay 99 is energized to close contactor 100 for energizing the blower windings 101. At the end of this condition, the timer 84 energizes a special control relay coil 102 which opens its normally closed contacts 103 to shut off control voltage. This enables all timers to fully reset. Coil 102 is a time delay device, so that contacts 103 will reclose to establish a start condition for a new cycle of operation. There is also shown in the power circuit portion of FIG. 19 a circuit breaker 104 which leads to individual manually operated devices such as the heat lamps 33, the illumination lamps 58 and a water switch and heating coil in the steam generator 41.

The invention provides an automatic, switching control over a variety of different conditions, or environments in a bathing chamber. The user can determine, and pre-select the duration of each condition. If he desires, any particular condition can be omitted by setting the respective timer for zero time. By providing a decking for a prone position the elements in the chamber ceiling are disposed to produce a substantially even effect over the entire body, as illustrated in FIG. 17. The apparatus is also used in a relaxing position for full synergy of the several bathing conditions.

The stereo sound, the heat lamps which are turned on or off as the user elects, and the illuminating lights 58 are all controlled separately from the automatic sequence, to set the mood and general temperature the user may select. These items can also be sequenced automatically, and by rearrangement of the control circuit the various environment conditions may be changed in sequence or variety.

The bathing chamber accommodates the user in a prone position, so that uniform light radiation, and uniform showering can be had over the entire body. This eliminates partial exposure of the body to the environmental conditions, as is usually the case in shower equipped apparatus. The prone position also permits overall body relaxation to increase the effects of the sequenced bathing conditions. To achieve the prone position, the apparatus provides a base stand 3 with a drainage flooring of approximately knee-height upon which the user can conveniently enter. The base stand 3 thus sits upon the ground surface, i.e. the flooring of the room in which the apparatus is installed, and the chamber rises upwardly from this base. The front panel 1 masks this construction when the apparatus is fully installed. The apparatus also makes use of sloping ceilings that drain off condensation to the rear and front chamber walls, thus reducing any dripping on the occupant that might otherwise occur.

While the chamber of the invention has been described as composed of teak wood walls, they could also be made of other materials, and synthetics have hereinbefore been suggested. Whatever the material, it is of advantage to have individual walls, ceiling, flooring and front, so that less space is required for shipment, and component parts can be more easily brought to the place of installation. Thus, as an alternative to the teak construction, the walls, ceiling, and flooring could be individually molded of synthetics with flanges on each that are abutted, gasketed, and bolted to one another to form a unitary whole.

A further modification may be the elimination of the base stand 3 as an integral part of the chamber. The shallow flooring may be reinforced as a stable component, which can be mounted on a stand constructed at the site of installation, and function as support for the walls and front. The flooring would preferably be at about knee-height, as in the embodiment of the drawings.

There is thus provided a bathing chamber with a flooring of a length to receive an occupant in the full prone position, i.e. flat or prostrate, a plurality of body conditioning elements, and a control system to automatically sequence the use of such elements in which individual timers may be set for the elements. The flooring may provide a drainage surface, and include a decking overlying such surface. There is thus provided a bathing chamber that is inviting, restful, invigorating, comfortable and enjoyable to use as an everyday convenience.

I claim:

1. In a bathing chamber the combination comprising:
an elongate enclosure having a ceiling, sides and an entry door with a lower sill extending along one lengthwise side;
a decking alongside said lower sill that extends across the length and width of the enclosure to support a user in prone and sitting positions with freedom of movement thereon;
an array of downwardly directed lamps associated with said ceiling and disposed above said decking to radiate downward with substantially uniform coverage of the decking; and
water sprays associated with said ceiling disposed above said decking to substantially uniformly shower the area of the decking.

2. A bathing chamber as in claim 1 having a control circuit with switching means for automatically sequencing the operation of said lamps and water sprays, and such switching means including individually preadjustable timing means for each of the lamps and water sprays.

3. In a bathing chamber the combination comprising:
an elongate enclosure having a ceiling and sides with an entry door along one lengthwise side;
a decking extending across the length of the enclosure to support a user in a prone position;
an array of downwardly directed lamps associated with said ceiling and disposed above said decking to radiate downward with substantially uniform coverage of the decking;
water sprays associated with said ceiling disposed above said decking to substantially uniformly shower the area of the decking;
a steam generator with an inlet disposed beneath the surface of said decking; and
air circulating openings with blower means entering upon said enclosure from opposite ends in the elongate direction at a level above said decking to direct air flow over a user in said prone position.

4. A bathing chamber as in claim 3 having a control circuit with switching means for automatically sequencing the operation of said lamps, sprays, steam generator and blower means and also having adjustable timer means for each thereof.

5. In a bathing chamber the combination comprising:
an enclosure;
a surface extending across the interior of said enclosure upon which a user may recline, sit and move about;
fluid emitting means entering upon said enclosure that directs fluid over said surface;
lamp sources within said enclosure directed toward said surface to radiate over the same;
air circulating means having openings with associated blower means entering upon said enclosure and positioned to direct air across said surface;
control means for individually operating said fluid emitting means, said lamp sources, and said air circulating means; and
switching in said control means that successively activates first said lamp sources, then said fluid emitting means and lastly said air circulating means.

6. In a bathing chamber the combination comprising:
a. an elongate drain flooring elevated above ground level with a water drainage outlet;
b. a base framework supporting said drain flooring in said elevated position;
c. a front panel extending along a lengthwise side of said flooring and rising from ground level to a height above said flooring, with an entry door positioned above said flooring;
d. a rear panel extending along the opposite lengthwise side of said flooring rising upward from said flooring to present a wall facing said front panel.
e. a pair of end panels rising upward from the ends of said flooring and extending between the front and rear panels to present a four sided enclosure;
f. a ceiling enclosing the top of the enclosure to form an enclosed chamber with said flooring and said front, rear and end panels;
g. a deck overlying said flooring to receive a person in prone position;
h. a steam injector entering said chamber and opening therein at a point beneath the upper surface of said deck;
i. air blowers with outlets opening into said chamber through said end panels at a level above said deck;
j. water sprays in said chamber that are directed downward toward said deck; and
k. lamps located in said chamber that are directed downward toward said deck.

7. A bathing chamber as in claim 6 with said water sprays and said lamps being located in the ceiling of said enclosure.

8. In a bathing chamber the combination comprising:
a. a base stand for resting upon a ground surface;
b. a drainage tray forming a chamber flooring supported upon said base stand at an elevated position, and a length and width to accept a person;
c. a decking overlaying said flooring upon which a person may move about;
d. chamber walls rising upward from said flooring;
e. a ceiling extending between said chamber walls overlying said flooring;
f. doors along one side of said flooring with a bottom sill at the level of and extending alongside said decking;
g. a plurality of chamber conditioning means arranged in said chamber to provide illumination, shower, and drying air, each means having an electrical control; and
h. a control circuit for operating said conditioning means in timed relation to each other.

9. In a bathing chamber the combination comprising:
a. a base stand;
b. a chamber flooring supported upon said base stand at an elevated position, and with a length and a width to accept a person in a prone position;
c. chamber walls rising upward from said flooring;
d. a chamber ceiling;
e. doors along one side of said chamber;
f. a light transmitting panel in one of said chamber walls allowing light passage therethrough;
g. a steam generator with a steam inlet entering said chamber;
h. blower means with air inlets in said chamber walls at a level to circulate air across the body surface of a person prone on said flooring;
i. a bank of lamps in said chamber directed toward said flooring;
j. shower nozzles mounted in said chamber that shower said flooring; and
k. a control circuit adapted to sequentially operate said steam generator, blower means, lamps and shower nozzles.

10. In a bathing chamber the combination comprising:
a. a base stand including a framework for resting upon a ground surface;
b. an elongate chamber flooring supported upon said base stand of configuration to accept a person in a prone position;
c. chamber rear and end walls rising upwardly from said flooring;
d. said rear and end walls having reinforcing along the outside surfaces thereof that extend downward beneath said flooring for attachment to said base stand;
e. a ceiling extending between said rear and end walls with sloping panels;

f. doors along the side of said flooring opposite said rear wall;

g. a front panel framing said doors and masking said side walls, ceiling, and base stand;

h. a steam generator beneath said flooring with a steam inlet entering said chamber;

i. blower means with warm air inlets at a level above said flooring to blow air across the body surface of a person in said chamber;

j. a bank of lamps in the upper region of the chamber directed downward to radiate uniformly over said flooring; and k. water spray nozzles mounted in said sloping ceiling panels that shower said flooring.

11. In a bathing chamber the combination comprising:

a. a base stand including a framework for resting upon a ground surface;

b. a drainage tray forming a chamber flooring supported upon said base stand at an elevated position, said tray being of elongate configuration with a length and a width to accept a person in a prone position;

c. chamber rear and end walls rising upwardly from said drainage tray;

d. said rear and end walls having reinforcing along the outside surfaces thereof that extends downward beneath said drainage tray and is attached to said base stand;

e. a ceiling extending between said rear and end walls overlying said drainage tray, with inwardly and upwardly sloping panels that peak toward a horizontal central panel running along the lengthwise ridge of said ceiling;

f. sliding doors along a lengthwise of said drainage tray to complete an enclosed chamber with said tray, side and rear walls, and ceiling;

g. a front panel framing said doors that extends beyond said side walls and down to a flooring to skirt said base stand;

h. a deck overlying said drainage tray adapted to support a person in a prone position;

i. a steam generator beneath said drainage tray and within said base stand, and having a steam inlet entering said chamber;

j. warm air inlets in said side walls at a level above said deck at a height substantially aligned with the upper body surface of a person prone on said deck;

k. a bank of ultra violet lamps spaced lengthwise of said chamber in said ceiling central panel directed downward to radiate upon said deck;

l. a plurality of infra-red heat lamps in each of said sloping ceiling panels directed downward to radiate upon said deck;

m. water spray nozzles mounted in said sloping ceiling panels interdigited with said heat lamps in an array that uniformly showers said deck; and n. a light transparent panel in a wall of the chamber with illumination on the outside thereof.

12. In a bathing chamber the combination comprising:

a. a flooring at about knee-height of a length to receive a person in prone position;

b. chamber walls rising upward from said flooring to permit a person to move about within the chamber;

c. a ceiling extending between said chamber walls and overlying said flooring at a height to permit sitting or prone positions within the chamber;

d. said ceiling and walls being individually formed with abutting surfaces forming joints therebetween for assembly thereof into said chamber;

e. a front panel extending in front of said flooring, walls and ceiling to mask the same, and having a framed opening with a bottom ledge at the height of about that of said flooring;

f. a door closing said opening with a bottom sill at a level of about that of said flooring; and g. a plurality of conditioning means arranged in said chamber.

13. In a bathing chamber the combination comprising:

an enclosed chamber having a flooring, walls and ceiling within which a user can recline or move about, said chamber including a front panel with a door operable from both within and without the chamber;

a warm air blower having an outlet directed into said chamber for moving heated air across the body of a user of the chamber;

a vent for said chamber to relieve pressure build-up within the chamber;

a plurality of conditioning means within said chamber that provide a variety of bathing conditions; and automatic control means with a control panel outside said chamber that provides individual preselection and duration of operation of each of said blower and said conditioning means in a successive operation thereof.

* * * * *